(12) United States Patent
Sawachi

(10) Patent No.: US 8,016,747 B2
(45) Date of Patent: Sep. 13, 2011

(54) CAPSULE ENDOSCOPE CAPABLE OF PERFORMING STEREOSCOPIC IMAGING

(75) Inventor: Youichi Sawachi, Saitama-ken (JP)

(73) Assignee: FUJIFILM Corporation, Tokyo (JP)

( * ) Notice: Subject to any disclaimer, the term of this patent is extended or adjusted under 35 U.S.C. 154(b) by 1128 days.

(21) Appl. No.: 11/808,453

(22) Filed: Jun. 11, 2007

(65) Prior Publication Data
US 2008/0045789 A1 Feb. 21, 2008

(30) Foreign Application Priority Data
Jul. 6, 2006 (JP) .................................. 2006-187061

(51) Int. Cl.
*A61B 1/04* (2006.01)
(52) U.S. Cl. ........ 600/111; 600/166; 600/173; 600/176; 348/45
(58) Field of Classification Search .................. 600/109, 600/160, 111, 166, 176, 179, 173; 348/45
See application file for complete search history.

(56) References Cited

U.S. PATENT DOCUMENTS

| | | | | |
|---|---|---|---|---|
| 3,520,587 A | * | 7/1970 | Ouchi et al. ................... 359/376 |
| 4,651,201 A | * | 3/1987 | Schoolman ..................... 348/45 |
| 4,873,572 A | * | 10/1989 | Miyazaki et al. ............... 348/45 |
| 5,168,364 A | * | 12/1992 | Kondo et al. ............... 348/230.1 |
| 5,335,648 A | * | 8/1994 | Kozawa et al. ................ 362/572 |
| 5,689,365 A | * | 11/1997 | Takahashi ..................... 359/362 |
| 5,940,126 A | * | 8/1999 | Kimura .......................... 348/294 |
| 5,944,655 A | * | 8/1999 | Becker .......................... 600/166 |
| 5,976,076 A | * | 11/1999 | Kolff et al. .................... 600/166 |
| 6,450,950 B2 | * | 9/2002 | Irion ............................. 600/170 |
| 6,652,451 B2 | * | 11/2003 | Murata et al. ................. 600/118 |
| 6,720,988 B1 | * | 4/2004 | Gere et al. ....................... 348/45 |
| 6,767,321 B2 | * | 7/2004 | Czarnek et al. ............... 600/111 |
| 7,108,657 B2 | * | 9/2006 | Irion et al. .................... 600/110 |

(Continued)

FOREIGN PATENT DOCUMENTS
JP  A 5-015515  1/1993
(Continued)

OTHER PUBLICATIONS

Corresponding JPO Official communication, (Dec. 2009).

*Primary Examiner* — John P Leubecker
(74) *Attorney, Agent, or Firm* — Sheldon J. Moss; Chad M. Herring

(57) ABSTRACT

A capsule endoscope capable of implementing stereoscopic photography, with which protruding/recessed states are easily recognized, for a nearby subject. The capsule endoscope includes imaging devices for respectively imaging a common subject, a driving/sampling section which drives the imaging devices, focusing optical systems which correspond one-to-one with the imaging devices and focus subject images onto imaging regions of the corresponding imaging devices, and a control section which controls imaging operations of the imaging devices with the driving/sampling section. At least one of the focusing optical systems is inclined such that an optical axis direction thereof is oriented forward in a direction of imaging by the plurality of imaging devices and toward a perpendicular direction that passes through a central point between the imaging regions of the plurality of imaging devices.

29 Claims, 9 Drawing Sheets

U.S. PATENT DOCUMENTS

| | | | |
|---|---|---|---|
| 7,525,320 B2 * | 4/2009 | Takami | 324/555 |
| 7,625,338 B2 * | 12/2009 | Gilad et al. | 600/173 |
| 7,877,134 B2 * | 1/2011 | Glukhovsky | 600/476 |
| 2001/0007051 A1 * | 7/2001 | Nakashima | 600/179 |
| 2005/0234296 A1 * | 10/2005 | Saadat et al. | 600/129 |
| 2005/0272979 A1 * | 12/2005 | Pauker et al. | 600/173 |
| 2007/0142710 A1 * | 6/2007 | Yokoi et al. | 600/173 |
| 2007/0197875 A1 * | 8/2007 | Osaka | 600/173 |
| 2008/0045800 A2 * | 2/2008 | Farr | 600/179 |

FOREIGN PATENT DOCUMENTS

| | | |
|---|---|---|
| JP | A 9-327447 | 12/1997 |
| JP | 10-192233 A | 7/1998 |
| JP | 2002-306491 A | 10/2002 |
| JP | 2003-275171 A | 9/2003 |
| JP | 2004-275542 A | 10/2004 |
| JP | 2005-143991 A | 6/2005 |
| JP | 2006-68488 A | 3/2006 |
| JP | 2006-75300 A | 3/2006 |

* cited by examiner

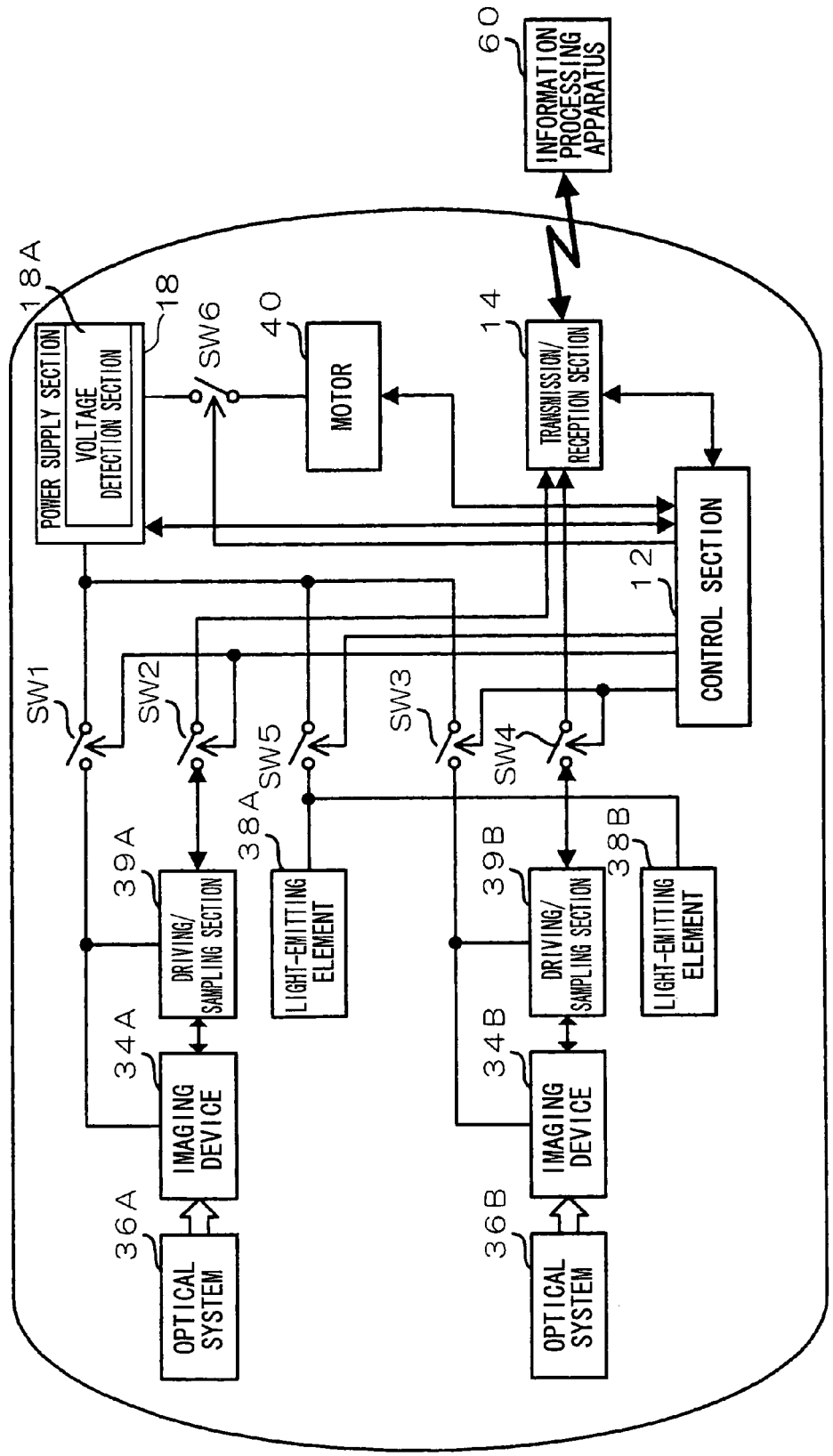

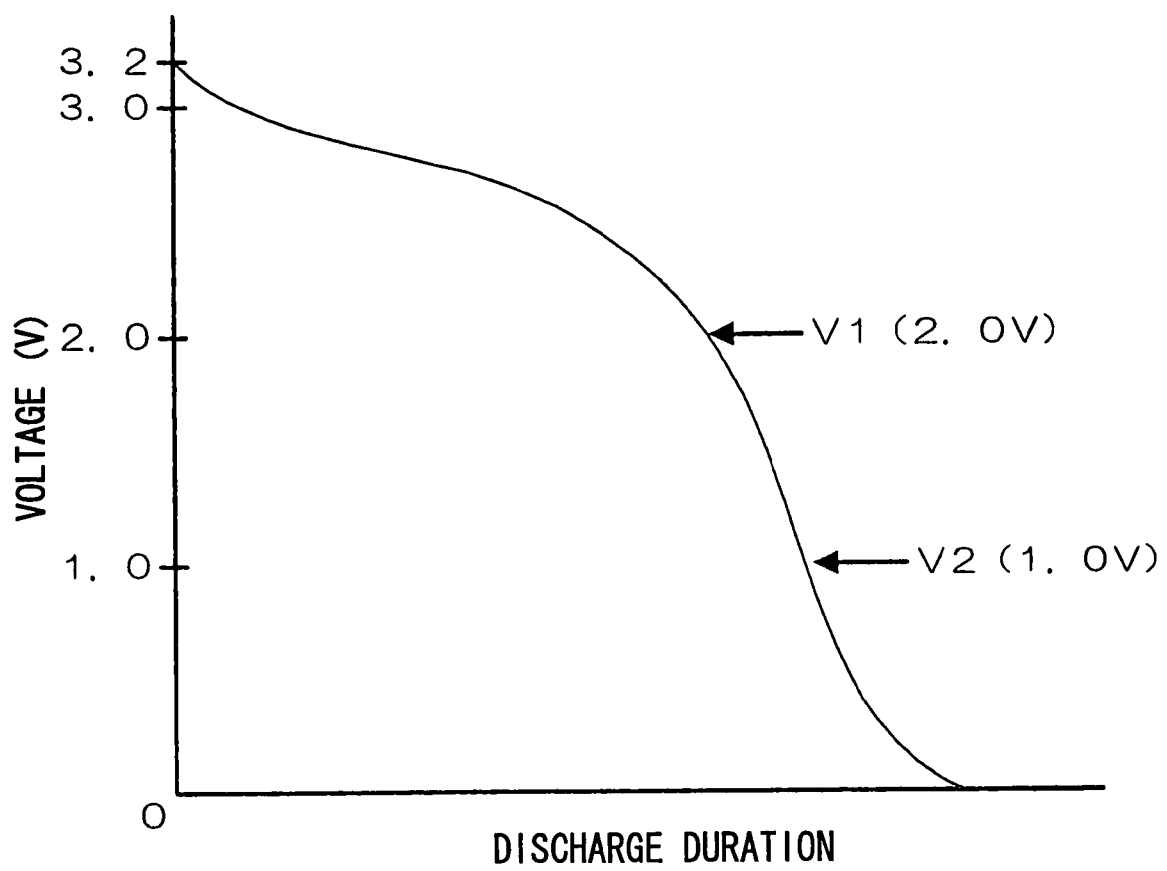
F I G. 3

F I G. 7A
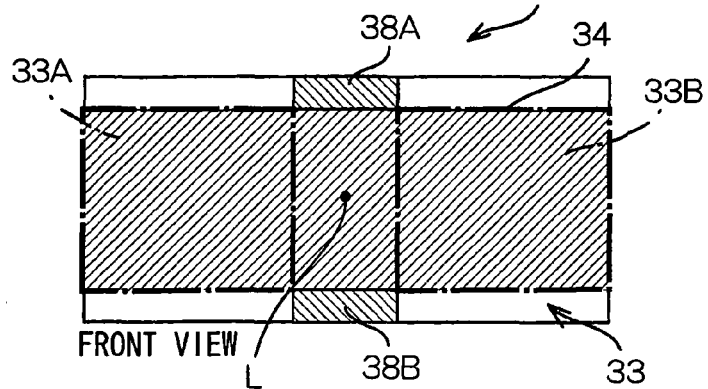
F I G. 7B
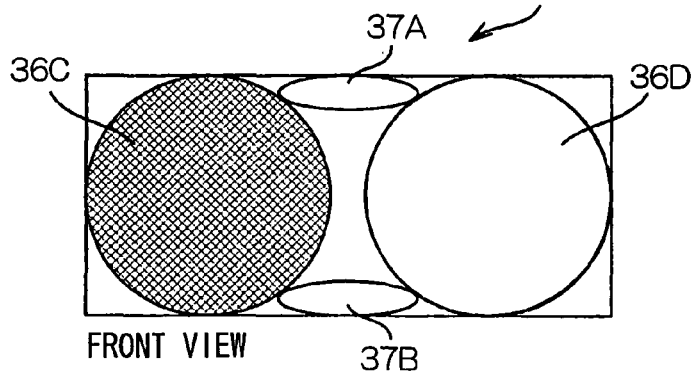
F I G. 7C
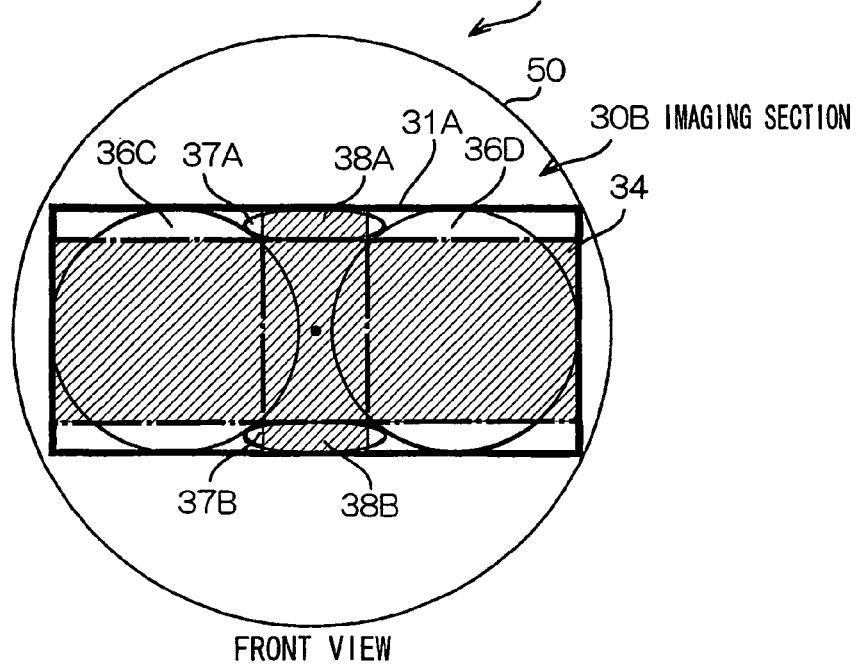

FRONT VIEW

FRONT VIEW

CAPSULE ENDOSCOPE CAPABLE OF PERFORMING STEREOSCOPIC IMAGING

CROSS-REFERENCE TO RELATED APPLICATION

This application claims priority under 35 USC 119 from Japanese Patent Application No. 2006-187061, the disclosure of which is incorporated by reference herein.

BACKGROUND OF THE INVENTION

1. Field of the Invention

The present invention relates to a capsule endoscope, and more particularly to a capsule endoscope capable of performing stereoscopic photography (multiple-lens photography).

2. Description of the Related Art

Heretofore, Japanese Patent Application Laid-Open (JP-A) No. 5-15515 has disclosed a technology which can be employed as a capsule endoscope, which is an ultra-small, capsule-type camera for body interior observation.

Furthermore, JP-A No. 9-327447 has disclosed a technology in which a medical-application capsule device equipped with sections with various functions includes: a generation section that includes a rotatably supported rotating member and generates electrical energy from rotation of this rotating member; an eccentric body fixed in a state which is eccentric relative to the rotating member; and an electricity storage section which stores power from the generation section and supplies power to the sections with various functions.

Now, the main purpose of a capsule endoscope is to find locations of abnormalities within the body. Therefore, for photography with a capsule endoscope, the ability to capture stereoscopic images at relatively close distances within the body is desirable. With stereoscopic images, protruding/recessed states at interior walls and the like are more easily recognized.

With the technologies disclosed in the aforementioned JP-A Nos. 5-15515 and 9-327447, stereoscopic photography can be realized by using plural capsules in an integrated structure. However, it is not necessarily always the case that stereoscopic photography, with which protruding/recessed states are easily recognized, can be performed on proximate subjects as described above, which is a problem.

SUMMARY OF THE INVENTION

The present invention has been devised in order to solve the problem described above, and will provide a capsule endoscope capable of performing stereoscopic photography, with which protruding/recessed states can be easily recognized on subjects which are nearby.

A first aspect of the present invention is a capsule endoscope including: a capsule housing; a plurality of imaging devices for respectively imaging a common subject; an imaging driving section that drives the plurality of imaging devices; a plurality of focusing optical systems that respectively correspond one-to-one with the plurality of imaging devices, each focusing optical system focusing an image of the subject at an imaging region of the corresponding imaging device; and a control section that controls an imaging operation of the plurality of imaging devices by the imaging driving section, wherein at least one of the plurality of focusing optical systems is inclined such that an optical axis direction thereof is oriented forward in a direction of imaging by the plurality of imaging devices and toward a perpendicular direction that passes through a central point between the imaging regions of the plurality of imaging devices.

According to the first aspect of the present invention, the plural imaging devices for respectively imaging the common subject are driven by the imaging driving section. At this time, the subject images are focused on the imaging regions of the plural imaging devices by the plural focusing optical systems that each correspond to one or other of the plural imaging devices. The imaging devices can include solid state imaging devices such as CCD area sensors, CMOS image sensors or the like.

Further, in the present invention, operations by the imaging driving section for imaging with the plural imaging devices are controlled by the control section.

In the present invention, at least one of the plural focusing optical systems is inclined such that the optical axis direction thereof is oriented both forward in a direction of imaging by the plural imaging devices and toward a perpendicular direction through the central point between the imaging regions of the plurality of imaging devices.

Thus, according to the first aspect of the present invention, the capsule endoscope includes: the capsule housing; the plural imaging devices for respectively imaging a common subject; the imaging driving section that drives the plural imaging devices; the plural focusing optical systems that respectively correspond one-to-one with the plural imaging devices, each focusing optical system focusing an image of the subject at the imaging region of the corresponding imaging device; and the control section that controls an imaging operation of the plural imaging devices by the imaging driving section, at least one of the plural focusing optical systems being inclined such that the optical axis direction thereof is oriented forward in the direction of imaging by the plural imaging devices and toward the perpendicular direction passing through the central point between the imaging regions of the plural imaging devices. Accordingly, it is possible to perform stereoscopic photography of a nearby subject with which protruding/recessed states can be easily recognized.

In the aspect described above, the capsule endoscope may further include: a rotating member provided so as to be rotatable about a predetermined rotation axis within the housing, the plural imaging devices being offset from the rotation axis and disposed at mutually different positions such that the plural imaging devices rotate about the rotation axis in accordance with rotation of the rotating member; and a rotation driving section that drives the rotation of the rotating member about the rotation axis, wherein the control section further controls a rotation operation of the rotating member by the rotation driving section. Accordingly, stereoscopic photography with which protruding/recessed states can be more easily recognized than in a case in which the plural imaging devices do not rotate can be performed.

In the aspects described above, the plurality of imaging devices may be provided within the housing such that central positions of the imaging regions are disposed at outer sides relative to optical axis centers of the corresponding focusing optical systems. Accordingly, stereoscopic photography of a nearby subject can be more favorably performed.

In the aspects described above, the imaging driving section may be plurally provided such that the imaging driving sections respectively correspond one-to-one with the plural imaging devices, the capsule endoscope may further include: a power supply section that supplies power to the plural image devices and the plural imaging driving sections to separately driving corresponding sets of the imaging devices and the imaging driving sections; and a detection section that detects a voltage of power supplied by the power supply section, and the control section may control such that an operation mode and a state of power supply from the power supply section are switched in accordance with a result of detection by the detection section. Accordingly, it is possible to perform excellent operations and power supply control in accordance with a power supply voltage.

In the aspect described above, the control section may control the power supply section such that, if the voltage detected by the detection section is higher than a predetermined threshold, power is supplied to all of the imaging devices and imaging driving sections and, if the detected voltage is less than or equal to the predetermined threshold, power is supplied to the respective sets of the imaging devices and the imaging driving sections in time divisions, and the control section may further control such that if the voltage detected by the detection section is less than or equal to a second predetermined threshold, which is lower than the predetermined threshold, power is supplied to only one of the sets of the imaging devices and the imaging driving sections. Accordingly, it is possible to perform excellent power supply control in accordance with a power supply voltage.

In the aspects described above, the capsule endoscope may further include a transmission section that transmits to outside the capsule endoscope information representing an operation mode that is being employed. Accordingly, the operation mode that is being employed can be ascertained by an external apparatus.

In the aspects described above, the capsule endoscope may further include a reception section that receives instruction information instructing an operation mode to be employed, wherein, when the instruction information is received by the reception section, the control section implements a control to switch the operation mode and state of power supply to the operation mode whose employment is instructed by the instruction information. Accordingly, operation modes and power supply conditions can be switched by an external apparatus, and usability can be improved.

In the aspects described above, the plural imaging devices may be integrally structured. Accordingly, reductions in size and costs are possible.

In the aspect described above, the integrally structured plural imaging devices may feature mutually different imaging sensitivity ranges. Accordingly, stereoscopic photography can be realized with plural mutually different imaging sensitivity ranges.

In the aspect described above, at least one of the different imaging sensitivity ranges may include a sensitivity range of non-visible light. Accordingly, stereoscopic photography can be realized with non-visible light.

In the aspects described above, the capsule endoscope may further include a light-emitting element that irradiates light at the subject. Accordingly, brightness of the subject can be made favorable.

In the aspect described above, the capsule endoscope may further include at least one of a condensing section that condenses light emitted from the light-emitting element toward the subject or a diffusion section that diffuses light emitted from the light-emitting element toward the subject. Accordingly, light can be more favorably illuminated onto the subject.

In the aspect described above, the focusing optical systems and the condensing section or diffraction section may be integrally structured. Accordingly, reductions in size and costs are possible.

In the aspects described above, the control section may control the rotation driving section so as to drive the rotating member to rotate within a range of rotation angle of 180°.

Accordingly, all photographic angles can be covered while stereoscopic photography is being performed, while if there is any wiring from the rotating member to other portions, excessive twisting of the wiring can be prevented.

In the aspects described above, the rotating member may include a circuit board including a circular form, the imaging devices being disposed at vicinities of end portions of the circuit board, or the plural imaging devices may be two imaging devices, with the rotating member having a circuit board including a rectangular form, at one end portion of which one of the imaging devices is disposed and at another end portion of which the other of the imaging devices is disposed, edges of the one end portion and the other end portion substantially matching lengths of corresponding edges of the imaging devices. Accordingly, the imaging devices can be disposed close to an outer surface of the main body, and hence photography of closer subjects can be performed.

According to the present invention, stereoscopic photography with which protruding/recessed states can be easily recognized can be applied to proximate subjects.

BRIEF DESCRIPTION OF THE DRAWINGS

Preferred exemplary embodiments of the present invention will be described in detail based on the following figures, wherein:

FIG. 2 is a block diagram showing principal structures of an electronic system of the capsule endoscope relating to the first embodiment;

FIG. 3 is a graph showing an example of a discharging characteristic of a button battery that is employed as a power source of a power supply section in the capsule endoscope relating to the first embodiment;

FIG. 7A is a front view showing structure of a circuit board employed by a control section of a capsule endoscope relating to a second embodiment;

FIG. 7B is a front view showing structure of an optics unit employed by the control section of the capsule endoscope relating to the second embodiment;

FIG. 7C is a front view showing overall structure of an imaging section of the capsule endoscope relating to the second embodiment;

DETAILED DESCRIPTION OF THE INVENTION

Herebelow, embodiments of the present invention will be described in detail with reference to the drawings.

First Embodiment

Figure 1A:
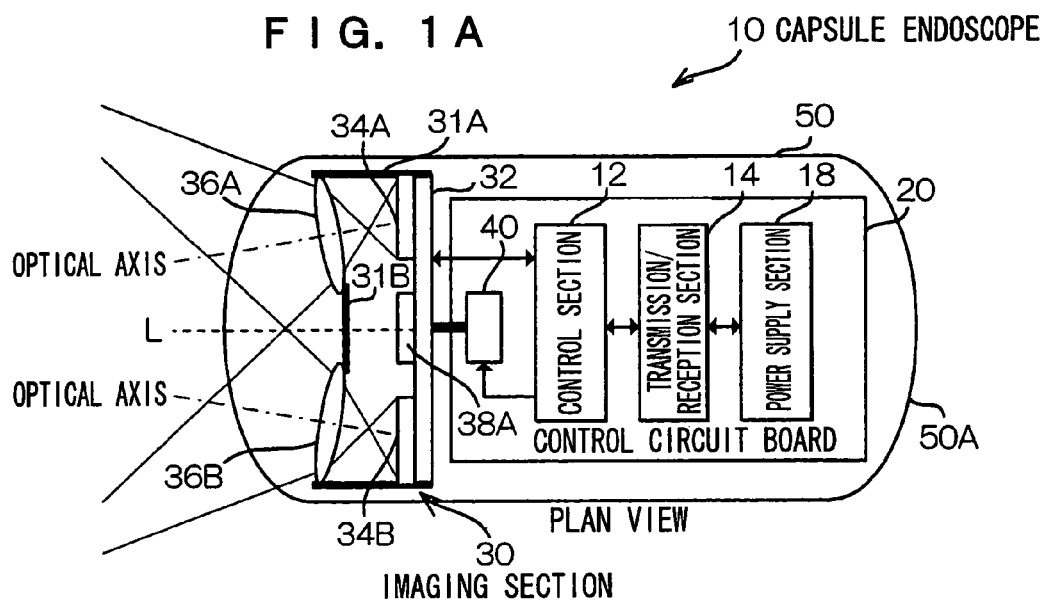
FIG. 1A is a (partially sectional) plan view showing overall structure of a capsule endoscope relating to a first embodiment.
Figure 1B:
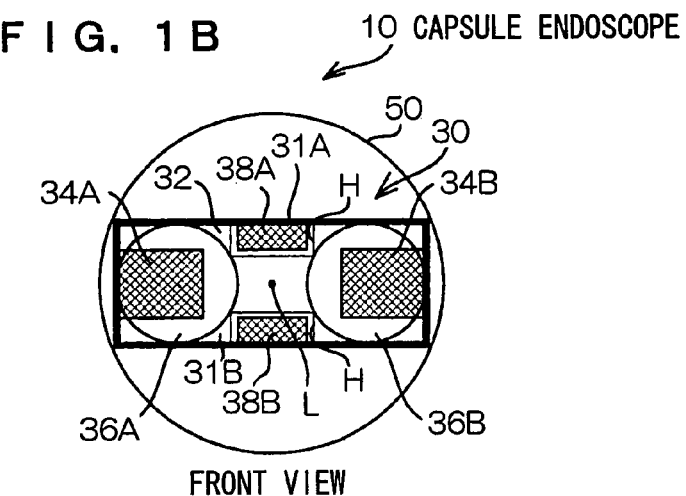
FIG. 1B is a front view showing the overall structure of the capsule endoscope relating to the first embodiment, showing the capsule endoscope in a state in which respective imaging sections are at different rotation angles.
Figure 1C:
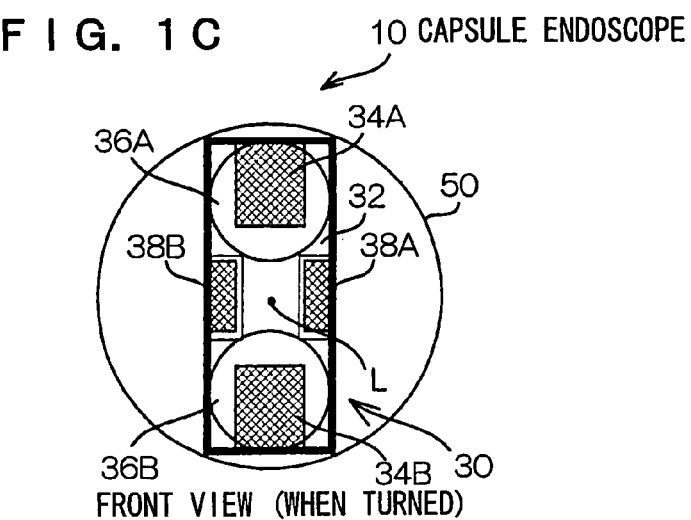
FIG. 1C is a front view showing the overall structure of the capsule endoscope relating to the first embodiment, showing the capsule endoscope in a state in which the respective imaging sections are at different rotation angles.

First, overall structure of a capsule endoscope 10 relating to the present embodiment will be described with reference to FIG. 1A to FIG. 1C. FIG. 1A is a plan view (partially sectional) of the capsule endoscope 10, and FIG. 1B and FIG. 1C are front elevation views of the capsule endoscope 10 in states with different rotation angles of an imaging section 30, which will be described later.

The capsule endoscope 10 relating to the present embodiment is formed to be enclosed by a capsule wall 50. A control circuit board 20, which administers overall operations of the capsule endoscope 10, and the imaging section 30, which captures images of subjects, are provided inside the capsule wall 50. For the capsule endoscope 10 relating to the present embodiment, a form with a cylindrical shape is employed as the capsule wall 50, one end of which has a hemispherical form and the other end of which is open, with the opening being closed off by a hemispherical cap 50A being attached thereto. However, this is not limiting; the form could be, for example, a spherical form, a form with an elliptical cross-section or the like, and modes in which other forms are employed are possible.

The imaging section 30 is equipped with a circuit board 32, a plurality (two in the present embodiment) of imaging devices 34A and 34B, a focusing optical system 36A and a focusing optical system 36B. The imaging device 34A and imaging device 34B are for respectively imaging a common subject. The focusing optical system 36A focuses a subject image onto an imaging region of the imaging device 34A, and the focusing optical system 36B focuses a subject image onto an imaging region of the imaging device 34B.

Here, CCD area sensors are employed as the imaging device 34A and imaging device 34B for the capsule endoscope 10 relating to the present embodiment, but it is possible to employ other imaging devices such as, for example, CMOS image sensors or the like. Further, single focusing lenses alone are employed for each of the focusing optical system 36A and the focusing optical system 36B in the capsule endoscope 10 relating to the present embodiment. However, modes in which, for example, a mechanism for focus adjustment, a mechanism for zooming or the like is provided in addition to a focusing lens to serve as the focusing optical system 36A or focusing optical system 36B, and thus functions for focus adjustment, zooming and the like can be included.

The circuit board 32 is provided to be rotatable about a pre-specified rotation axis L. In the capsule endoscope 10 relating to the present embodiment, a board with a rectangular shape in front view is employed as the circuit board 32, and the rotation axis L that is utilized is a center of gravity (a central position) of the circuit board 32.

The imaging device 34A and imaging device 34B are disposed at positions which are substantially symmetrical about the rotation axis L of the circuit board 32. A light-emitting element 38A and a light-emitting element 38B, which emit light at subjects, are provided at two positions which are substantially symmetrical on a perpendicular line which intersects a straight line joining the positions of arrangement of the imaging device 34A and imaging device 34B. Herein, "substantially symmetrical" means point symmetry with tolerance for errors which are unavoidable, such as errors in fabrication, errors which arise due to changes in environmental conditions, errors due to changes over time and so forth. For the capsule endoscope 10 relating to the present embodiment, light-emitting diodes are employed as the light-emitting elements 38A and 38B, but this is not limiting and other light-emitting bodies may be employed, such as miniature light bulbs, organic EL elements or the like.

An outer periphery wall 31A is provided at the circuit board 32, standing along an outer peripheral portion thereof, and the focusing optical system 36A and focusing optical system 36B are disposed at an opposite edge of the outer periphery wall 31A from an edge thereof at which the circuit board 32 is disposed. Here, the focusing optical system 36A and focusing optical system 36B both have circular forms in front view. Space between outer periphery portions of the focusing optical systems and the outer periphery wall 31A is covered by a front face wall 31B, which is provided with opening portions H. Thus, the imaging section 30 is formed in a substantially rectangular solid shape, which is substantially closed, by the circuit board 32, the outer periphery wall 31A, the focusing optical systems 36A and 36B, and the front face wall 31B.

The opening portions H are provided at two locations of the front face wall 31B, corresponding to directions of progress of light irradiated from the light-emitting element 38A and the light-emitting element 38B, and the radiated light is illuminated at the subject through the opening portions H.

The focusing optical system 36A and the focusing optical system 36B are inclined such that optical axis directions thereof are oriented to forwards in directions of imaging by the imaging devices 34A and 34B and also towards a perpendicular direction that passes through a center point between the respective imaging regions of the imaging devices 34A and 34B (i.e., the axial direction of the rotation axis L). Thus, stereoscopic imaging of a subject that is nearby can be excellently implemented.

The control circuit board 20 is fixed inside the capsule wall 50 and is provided with a control section 12, a transmission/reception section 14, a power supply section 18 and a motor 40. The control section 12 administers overall operations of the capsule endoscope 10. The transmission/reception section 14 administers communication operations with an external apparatus which is, for example, an information processing apparatus 60 as shown in FIG. 2 (here, a personal computer) or the like. The power supply section 18 supplies electrical power for driving to various sections in the capsule endoscope 10. The motor 40 drives rotation of the circuit board 32 (the imaging section 30) about the rotation axis L.

The motor 40 is mounted with a rotation axis thereof at the rotation axis L of the circuit board 32, and fulfils the function of driving rotation of the imaging section 30. In the capsule endoscope 10 relating to the present embodiment, a stepper motor is employed as the motor 40. However, the motor 40 is not limited to being a stepper motor and other motors such as, for example, a DC motor, an ultrasonic motor or the like may be employed. However, for the capsule endoscope 10, employment of a stepper motor is preferable, for positioning a rotation angle of the imaging section 30 at a required angle with high accuracy.

Furthermore, in the capsule endoscope 10 relating to the present embodiment, equipment which performs wireless communications in compliance with a predetermined wireless standard is employed as the transmission/reception section 14. As the power supply of the power supply section 18 in the capsule endoscope 10 relating to the present embodiment, a button battery structured as a primary cell is employed. However, the power supply section 18 is not limited to a button battery; a mode which employs another battery such as a secondary cell or the like, a mode in which electric power is supplied by electromagnetic induction from outside, and the like are possible.

Next, principal structures of an electronic system of the capsule endoscope 10 relating to the present embodiment will be described with reference to FIG. 2.

As shown in FIG. 2, a driving/sampling section 39A and a driving/sampling section 39B are provided in the capsule endoscope 10. The driving/sampling section 39A is provided in correspondence with the imaging device 34A, drives the imaging device 34A and outputs image data, which represents a subject image that is outputted from the imaging device 34A as a result of the driving, as a sampling signal. The driving/sampling section 39B is provided in correspondence with the imaging device 34B, drives the imaging device 34B and outputs image data, which represents a subject image that is outputted from the imaging device 34B as a result of the driving, as a sampling signal. The capsule endoscope 10 is further provided with six switches SW1 to SW6. Control terminals of the control section 12 are electrically connected with the switches SW1 to SW6. The switches SW1 to SW6 implement connection/disconnection (opening and closing operations) between pairs of terminals in accordance with control signals inputted through the control terminals.

The driving/sampling sections 39A and 39B and the switches SW1 to SW5 may be disposed at either of the circuit board 32 and the control circuit board 20, but are disposed at the control circuit board 20 in the capsule endoscope 10 relating to the present embodiment. The switch SW6 is disposed at the control circuit board 20. Communications of various signals between various sections disposed at the circuit board 32 and various sections disposed at the control circuit board 20 are implemented by wiring. Accordingly, the rotation angle of the imaging section 30 is limited to within a range from 0° to 180°, with 0° being a predetermined reference angle.

A power supply terminal of the power supply section 18 is electrically connected, via the switch SW1, to an input terminal at which power is inputted for driving the imaging device 34A and the driving/sampling section 39A. Thus, the control section 12 can control to supply and halt supply of power for driving to the imaging device 34A and the driving/sampling section 39A.

Further, the driving/sampling section 39A is electrically connected to the imaging device 34A and is electrically connected, via the switch SW2, to the transmission/reception section 14. Thus, when the switch SW2 is switched to the connected state, the image data which has been sampled by the driving/sampling section 39A can be transmitted to the outside via the transmission/reception section 14.

The control terminals for the switch SW1 and the switch SW2 are electrically connected to the control section 12 by a common connection line. Therefore, the control section 12 can implement control of a state of power supply to the imaging device 34A and the driving/sampling section 39A and control of connection/disconnection between the driving/sampling section 39A and the transmission/reception section 14 with a single control signal.

Similarly, the power supply terminal of the power supply section 18 is electrically connected, via the switch SW3, to an input terminal at which power is inputted for driving the imaging device 34B and the driving/sampling section 39B. Thus, the control section 12 can control to supply and halt supply of power for driving to the imaging device 34B and the driving/sampling section 39B.

Further, the driving/sampling section 39B is electrically connected to the imaging device 34B and is electrically connected, via the switch SW4, to the transmission/reception section 14. Thus, when the switch SW4 is switched to the connected state, the image data which has been sampled by the driving/sampling section 39B can be transmitted to the outside via the transmission/reception section 14.

The control terminals for the switch SW3 and the switch SW4 are electrically connected to the control section 12 by a common connection line. Therefore, the control section 12 can implement control of a state of power supply to the imaging device 34B and the driving/sampling section 39B and control of connection/disconnection between the driving/sampling section 39B and the transmission/reception section 14 with a single control signal.

The power supply terminal of the power supply section 18 is also electrically connected, via the switch SW5, to input terminals for inputting power for driving the light-emitting element 38A and the light-emitting element 38B (i.e., for light emission). Thus, the control section 12 can control to supply and halt supply of power for driving to the light-emitting element 38A and the light-emitting element 38B. It is further possible to regulate the light by switching the switch SW5 with arbitrary periods, and this can be utilized for exposure control, energy-saving operations and the like.

The power supply terminal of the power supply section 18 is also connected, via the switch SW6, to an input terminal for inputting power for driving rotation of the motor 40. Thus, the control section 12 can control to supply and halt supply of power for driving to the motor 40.

The control section 12 is also electrically connected to a control terminal of the motor 40. Hence, the control section 12 implements control of operations (rotation driving) of the motor 40. The control section 12 is yet further electrically connected to control terminals of both the power supply section 18 and the transmission/reception section 14. Thus, operations of the power supply section 18 and the transmission/reception section 14 are also controlled by the control section 12.

As is also shown in FIG. 2, a voltage detection section 18A is provided at the power supply section 18. The voltage detection section 18A senses a voltage value of power that is supplied by the power supply section 18. Thus, the control section 12 can ascertain the voltage value.

Switching of an operation mode of the capsule endoscope 10 relating to the present embodiment can be instructed by the information processing apparatus 60 (here, a personal computer), which is equipped with functions enabling wireless communications in compliance with the communications standard with which the transmission/reception section 14 complies.

In the capsule endoscope 10 relating to the present embodiment, four operation modes—a full driving mode, an alternate driving mode, a single driving mode and a rotation driving mode—are prepared in advance as the operation modes. The full driving mode is an operation mode for driving all of imaging optical systems, which are structured by sets of a corresponding focusing optical system, imaging device and driving/sampling section, at the same time. The alternate driving mode is an operation mode for alternately driving a number (here, two) of these imaging optical systems one set at a time with predetermined timings (here, once each in a cycle of vertically synchronized signals of the imaging devices with the same period). The single driving mode is an operation mode for driving only one set of the imaging optical systems. The rotation driving mode is an operation mode for turning the imaging section 30 in an instructed direction (a direction which is either clockwise or counterclockwise) by a predetermined angle (here, 5°).

When performing driving in the full driving mode, the control section 12 sets all of the switches SW1 to SW6 to the connected state, and drives all the imaging optical systems simultaneously. At the same time, the control section 12 controls the various sections of the driving/sampling sections 39A and 39B and the transmission/reception section 14 so as to continuously transmit image data obtained by the imaging optical systems to the outside.

When performing driving in the alternate driving mode, the control section 12 sets the switch SW5 and the switch SW6 to the connected state, and at intervals of the aforementioned predetermined timings, alternately switches such that switches corresponding to the imaging optical system that is an object of driving are in the connected state (switch SW1 and switch SW2 for the imaging optical system including the imaging device 34A, and switch SW3 and switch SW4 for the imaging optical system including the imaging device 34B). In addition, the control section 12 controls the various sections of the driving/sampling sections 39A and 39B and the transmission/reception section 14 so as to continuously transmit image data obtained by the imaging optical system that is the object of driving to the outside.

When performing driving in the single driving mode, the control section 12 sets the switch SW5 and the switch SW6 to the connected state, sets the switches corresponding to the one imaging optical system that is an object of driving to the connected state, and controls the various sections of the driving/sampling section 39A or 39B and the transmission/reception section 14 so as to continuously transmit image data obtained by the imaging optical system that is the object of driving to the outside.

The image data that is transmitted from the capsule endoscope 10 in accordance with the respective operation mode as described above is received by the information processing apparatus 60. At the information processing apparatus 60, the image data is saved to a memory section, such as, for example, a hard disk device, main memory or the like provided at the information processing apparatus 60, and various kinds of processing for displaying the captured image at a display section, which is provided at the information processing apparatus 60, and the like are executed.

The capsule endoscope 10 is equipped with an operation mode-switching function which automatically switches the operation mode in accordance with the voltage value of the power supplied from the power supply section 18.

Now, in the capsule endoscope 10 relating to the present embodiment, the above-mentioned operation mode-switching function is a function which switches the operation mode in accordance with two thresholds, as shown by the example in FIG. 3: a voltage value V1 which is specified beforehand as a threshold (here, 2.0 V) that is a lower limit above which power can be supplied relatively stably; and a voltage value V2, which is lower than the voltage value V1 and is specified beforehand as a threshold (here, 1.0 volts) subsequent to which a duration over which power supply is possible is a predetermined period which is a relatively short period (here, 10 minutes). However, switching of the operation mode is not limited thus. Obviously, a mode which performs switching using only one threshold such as the voltage value V1 or the like, a mode which performs switching using three or more thresholds, with one or more thresholds provided in addition to the voltage value V1 and the voltage value V2, and so forth are possible.

Figure 4:
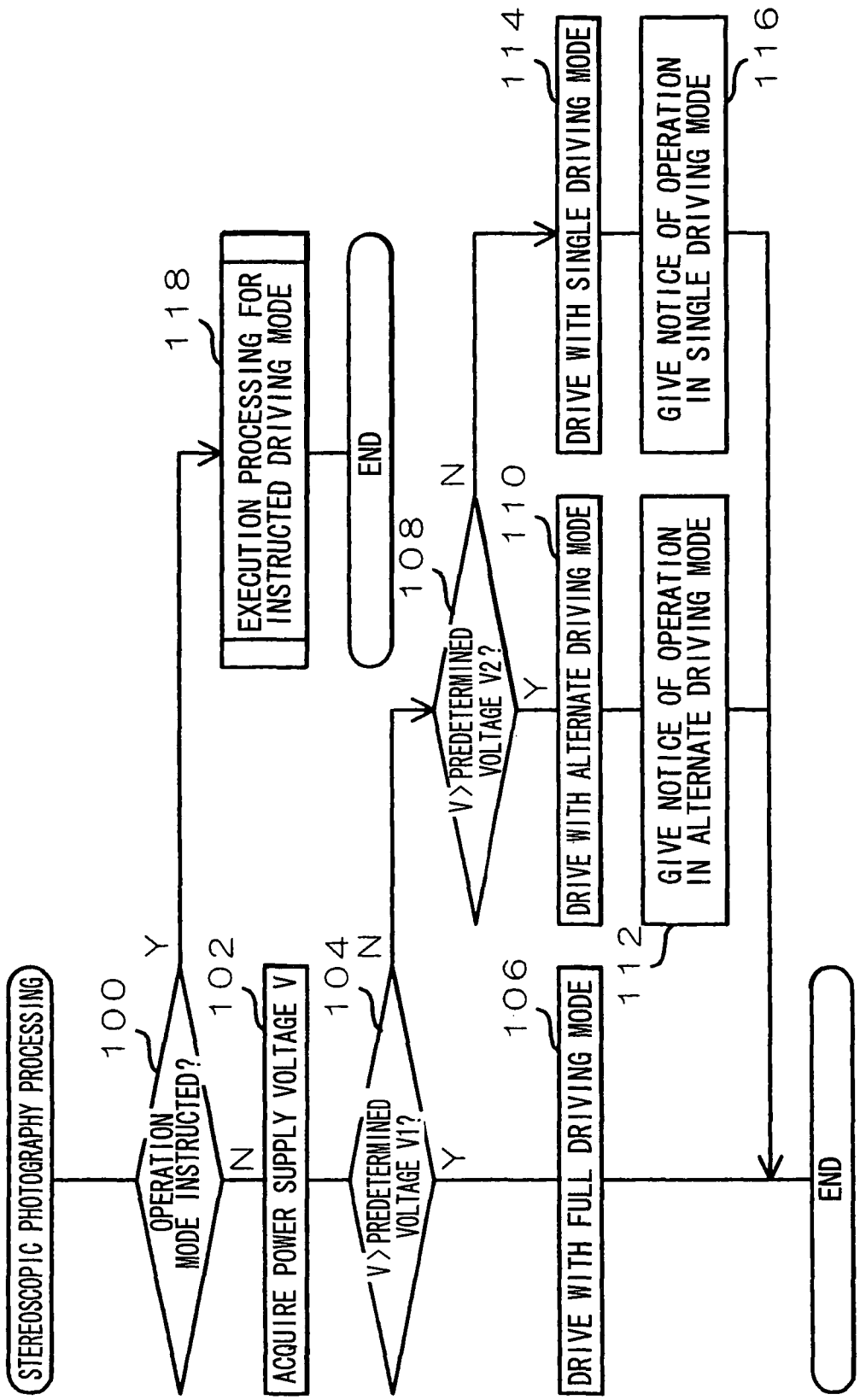
FIG. 4 is a flowchart showing a flow of processing of a stereoscopic photography processing program relating to the first embodiment.

Next, operation of the capsule endoscope 10 relating to the present embodiment will be described with reference to FIG. 4. FIG. 4 is a flowchart showing a flow of processing of a stereoscopic photography processing program which is executed by the control section 12 of the capsule endoscope 10 at intervals of a predetermined period (herein, one-second intervals). This program is memorized in advance at a memory (not illustrated) incorporated in the control section 12.

First, in step 100, it is determined whether or not instruction information instructing switching of the operation mode and information indicating an operation mode after the switching (here, information representing any one of the full driving mode, the alternate driving mode, the single driving mode and the rotation driving mode) have been received. If this determination is negative, it is considered that the operation mode-switching function is to be executed and the processing advances to step 102.

In step 102, a voltage value V sensed by the voltage detection section 18A is acquired from the power supply section 18. Then, in step 104, it is determined whether or not the voltage value V is larger than the voltage value V1. If this determination is positive, the processing advances to step 106.

In step 106, the various sections are controlled so as to drive in the full driving mode thereafter. Then, the stereoscopic photography processing program ends.

On the other hand, if the determination of step 104 is negative, the processing advances to step 108 and it is determined whether or not the voltage V is larger than the voltage V2. If this determination is positive, the processing advances to step 110.

In step 110, the various sections are controlled so as to drive in the alternate driving mode thereafter. Then, in step 112, information representing driving in the alternate driving mode is transmitted via the transmission/reception section 14. Then, the stereoscopic photography processing program ends.

Meanwhile, if the determination of step 108 is negative, it is considered that the voltage value V is lower than the voltage value V2, and the processing goes down to step 114. The various sections are controlled so as to drive in the single driving mode thereafter. Then, in step 116, information representing driving in the single driving mode is transmitted via the transmission/reception section 14. Then, the stereoscopic photography processing program ends.

On the other hand, if the determination of the aforementioned step 100 is positive, the processing advances to step 118, and the various sections are controlled so as to drive in the operation mode indicated by the received information thereafter. Then, the stereoscopic photography processing program ends. In step 118, if the operation mode indicated by the received information is the full driving mode, the alternate driving mode or the single driving mode, processing of a step the same as step 106, step 110 or step 114 is executed. However, if the operation mode indicated by the received information is the rotation driving mode, the motor 40 is controlled so as to turn the imaging section 30 in the designated rotation direction through a predetermined angle (here, 5°). Now, as mentioned earlier, rotation angles of the imaging section 30 in the capsule endoscope 10 relating to the present embodiment are limited to within a range from the predetermined reference angle to 180°. Therefore, when the imaging section 30 is to be turned, it is determined whether or not the rotation angle of the imaging section 30 will stay within the range, from the predetermined reference angle to 180°, if the imaging section 30 is turned by the predetermined angle in the instructed rotation direction from the rotation angle at this point in time. The imaging section 30 is only turned if the angle will stay within the range.

According to the stereoscopic photography processing program described above, the capsule endoscope 10 operates in a designated operation mode when an operation mode is instructed from the information processing apparatus 60, and in other cases operates according to the operation mode-switching function.

As has been described in detail hereabove, the present embodiment is provided with plural imaging devices for respectively imaging a common subject (here, the imaging devices 34A and 34B), imaging driving sections (here, the driving/sampling sections 39A and 39B) which drive the plural imaging devices, plural focusing optical systems (here, the focusing optical system 36A and 36B) which each correspond to one or another of the plural imaging devices and focus subject images onto imaging regions of the corresponding imaging devices, and a control section (here, the control section 12) which controls imaging operations of the plural imaging devices through the imaging driving sections. Because the focusing optical systems are inclined such that the optical axis directions thereof are oriented forwards in the directions of imaging by the plural imaging devices and towards the perpendicular direction passing through the central point between the imaging regions of the plural imaging devices, it is possible to perform stereoscopic imaging, with which protruding/recessed conditions are easily recognized, for a proximate subject.

Moreover, the present embodiment is provided with a rotating member (here, the imaging section 30), which is provided to be turnable about a predetermined rotation axis within the main body, with the plural imaging devices being offset from the rotation axis and disposed at mutually different positions such that the plural imaging devices turn about the rotation axis in accordance with turning of the rotating member, and a rotation driving section (here, the motor 40) which drives turning of the rotating member about the rotation axis. Because turning of the rotating member by the rotation driving section is also controlled by the control section, stereoscopic photography with which protruding/recessed portions are easily recognized can be more easily carried out than in a case in which the plural imaging devices do not turn.

Moreover, in the present embodiment, the imaging driving sections are plurally provided so as to correspond one-to-one with the plural imaging devices. Further, for the plural imaging devices and the plural imaging driving sections, a power supply section (here, the power supply section 18) which supplies power for driving separately to corresponding sets of an imaging device and an imaging driving section, and a detection section which senses a voltage of the power that is supplied by the power supply section (here, the voltage detection section 18A) are further provided. Because control is performed so as to switch an operation mode (here, the full driving mode, alternate driving mode, single driving mode or rotation driving mode) and a state of power supply by the power supply section in accordance with results of sensing by this detection section, excellent operations and power supply control can be implemented in accordance with power supply voltages.

Moreover, in the present embodiment, control is performed such that when a voltage sensed by the detection section is higher than a predetermined threshold (here, the voltage value V1), power is supplied to all the imaging devices and the imaging driver sections, and when the voltage is below the predetermined threshold, power is supplied to each of the sets of imaging devices and imaging driving sections in time divisions. Therefore, excellent power supply control in accordance with power supply voltages can be performed.

In particular, in the present embodiment, when the voltage sensed by the detection section is below a second predetermined threshold (here, the voltage value V2), which is lower than the predetermined threshold, control is performed such that power is supplied to only one set of an imaging device and an imaging driving section. Thus, more excellent power supply control in accordance with power supply voltages can be performed.

Moreover, in the present embodiment, because information indicating the operation mode that is being employed is transmitted to the outside, the operation mode can be ascertained by an external apparatus.

Moreover, the present embodiment is further provided with a reception section (here, the transmission/reception section 14) which receives instruction information designating an operation mode to be employed. When the instruction information is received by the reception section, control is performed to switch the operation mode and power supply state to the operation mode whose employment is instructed by the instruction information. Thus, switching of the operation mode and power supply state can be performed from an external apparatus, and usability can be improved.

Moreover, because the present embodiment is further provided with a light-emitting element which illuminates light at the subject (here, the light-emitting elements 38A and 38B), brightness of the subject can be set to an excellent brightness.

Furthermore, in the present embodiment, the rotation driving section is controlled so as to drive turning to rotation angles of the rotating member within a range of 180°. Therefore, if there are any wires from the rotating member to other portions, excessive twisting of the wires can be prevented while all photographic angles can be covered when stereoscopic photography is being carried out.

Figure 5:
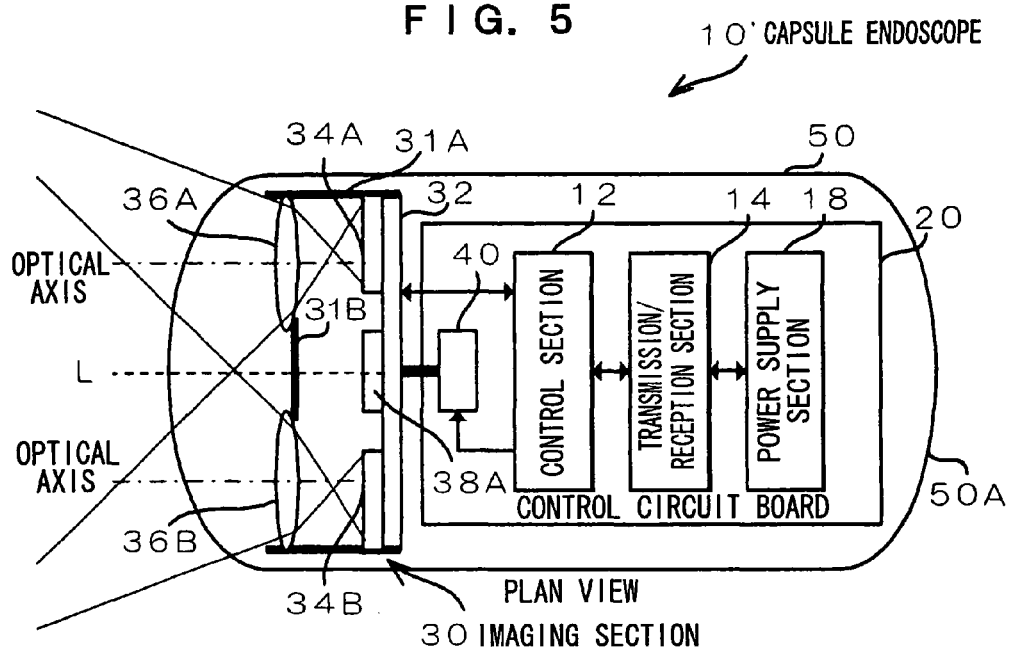
FIG. 5 is a (partially sectional) plan view showing overall structure of a variant example of the capsule endoscope relating to the embodiment.

In addition, for the present embodiment, a case has been described in which the focusing optical system 36A and the focusing optical system 36B are angled such that the respective optical axis directions thereof approach the axial direction of the rotation axis L at the forward side of the imaging directions according to the imaging devices 34A and 34B, in order to enable excellent performance of stereoscopic photography for a proximate subject. However, the present invention is not limited thus. As shown by the example in FIG. 5 (capsule endoscope 10'), it is possible to form a mode in which, rather than the focusing optical system 36A and focusing optical system 36B being angled, the imaging device 34A and imaging device 34B are disposed such that central positions of the imaging regions thereof are located at outer sides relative to the optical axis centers of the corresponding focusing optical systems. Correspondingly, stereoscopic photography can be excellently performed for a proximate subject.

Figure 6:
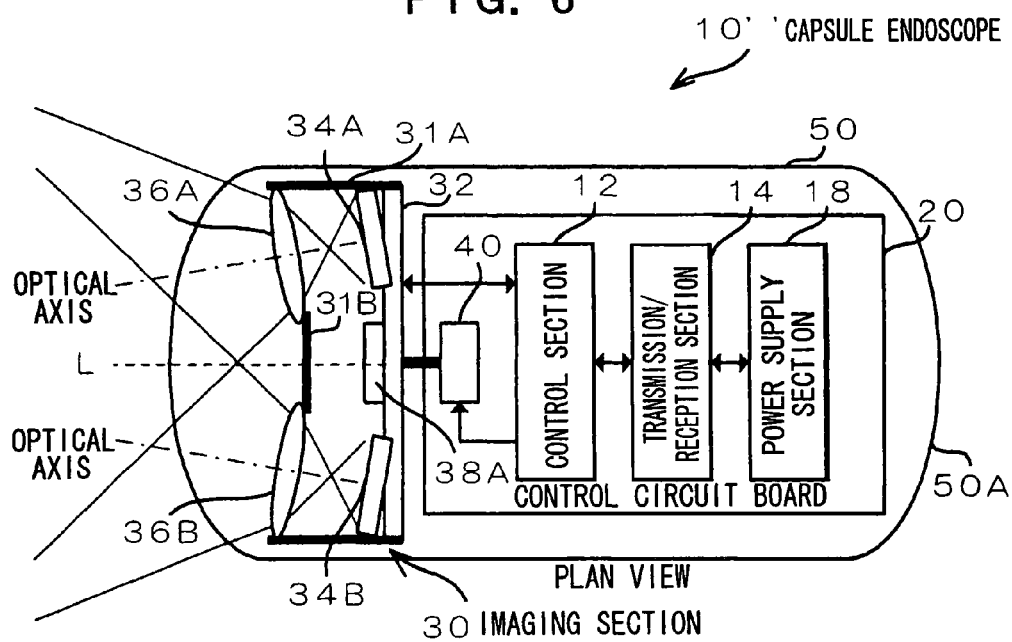
FIG. 6 is a (partially sectional) plan view showing overall structure of another variant example of the capsule endoscope relating to the embodiment.

Furthermore, for the present embodiment, a case has been described in which the imaging device 34A and imaging device 34B are disposed such that imaging faces thereof are aligned with an elevation plane of the capsule endoscope. However, the present invention is not limited thus. As shown by the example in FIG. 6 (capsule endoscope 10"), it is possible to form a mode in which the imaging device 34A and imaging device 34B are disposed at inclination angles the same as the corresponding focusing optical systems, such that central axis positions of the imaging regions coincide with optical axis positions of the corresponding focusing optical systems. In such a case, photography by the imaging devices with less distortion of the subject is possible.

Furthermore, for the present embodiment, a case has been described in which the two imaging devices 34A and 34B are employed as the plural imaging devices of the present invention. However, the present invention is not limited thus. Obviously, three or more imaging devices could be employed. In such a case, focusing optical systems and driving/sampling sections to the number of the imaging devices would be required in correspondence with the imaging devices. In such a case too, the same effects can be realized as with the present embodiment.

Second Embodiment

For this second embodiment, a variant example will be described, which is a case in which the plural imaging devices are formed in an integrated structure. Structure of a capsule endoscope 10B relating to this second embodiment is similar to the capsule endoscope 10 relating to the above-described first embodiment, except for structure of the imaging section. Accordingly, structure of an imaging section 30B relating to this second embodiment will now be described with reference to FIG. 7A to FIG. 7C.

As shown in FIG. 7A, a circuit board 32B which is utilized at the imaging section 30B has a rectangular shape in front view, similarly to the first embodiment. At the circuit board 32B, a single imaging device 34, of which a length direction length of the imaging region substantially matches a length direction length of the circuit board 32B, is disposed such that the center of an imaging region 33 coincides with the rotation axis L of the circuit board 32B. The light-emitting element 38A and light-emitting element 38B, which are similar to those of the first embodiment, are disposed at similar positions to the first embodiment. In the capsule endoscope 10B relating to the present embodiment, a CCD area sensor is employed as the imaging device 34, but another imaging device such as, for example, a CMOS image sensor or the like could be employed.

In the capsule endoscope 10B relating to the present embodiment, the imaging region 33 of the imaging device 34 is employed in a state of being divided into two regions with rectangular shapes which are located at positions with point symmetry with one another about the rotation axis L—an imaging region 33A and an imaging region 33B.

As ranges of wavelengths of detectable light of the imaging device 34 relating to the present embodiment, the imaging region 33A is structured to employ a visible wavelength range and the imaging region 33B is structured to employ a non-visible light region (here, an infrared light region). Correspondingly, the light-emitting element 38A relating to the present embodiment is structured to emit visible light and the light-emitting element 38B is structured to emit infrared light.

As shown in FIG. 7B, at the imaging section 30B relating to this second embodiment, a structure in which a focusing optical system 36C, a focusing optical system 36D, a condensing optical system 37A and a condensing optical system 37B are integrally formed of resin (for example, a plastic resin) is employed as an optics unit 35.

Here, the focusing optical system 36C is for focusing a subject image onto the imaging region 33A of the imaging device 34 and the focusing optical system 36D is for focusing a subject image onto the imaging region 33B of the imaging device 34. The focusing optical system 36C and the focusing optical system 36D are inclined such that respective optical axis directions thereof are oriented towards the direction of the rotation axis L at the forward side of a direction of imaging by the imaging device 34, and are similar to the focusing optical systems of the capsule endoscope 10 relating to the first embodiment. Thus, stereoscopic photography can be excellently implemented for a proximate subject. A surface of the focusing optical system 36C is subjected to IR-coating. As a result, it is possible to avoid adverse effects due to the infrared light emitted by the light-emitting element 38B at a subject image being captured by the imaging region 33A of the imaging device 34.

The condensing optical system 37A is for condensing the illumination light emitted from the light-emitting element 38A toward the subject, and the condensing optical system 37B is for condensing the illumination light emitted from the light-emitting element 38B toward the subject.

In the capsule endoscope 10B relating to this second embodiment, as shown in FIG. 7C, the circuit board 32B and the optics unit 35 which are structured as described above are employed to constitute the imaging section 30B, and the imaging section 30B is accommodated within the capsule wall 50 of the capsule endoscope 10 in a state substantially the same as the state illustrated in FIG. 1A to FIG. 1C.

Next, principal structures of an electronic system of the capsule endoscope 10B relating to this second embodiment will be described with reference to FIG. 8. Structural elements that are the same in FIG. 8 as in FIG. 2 are assigned the same reference numerals, and descriptions thereof will not be given.

Figure 8:
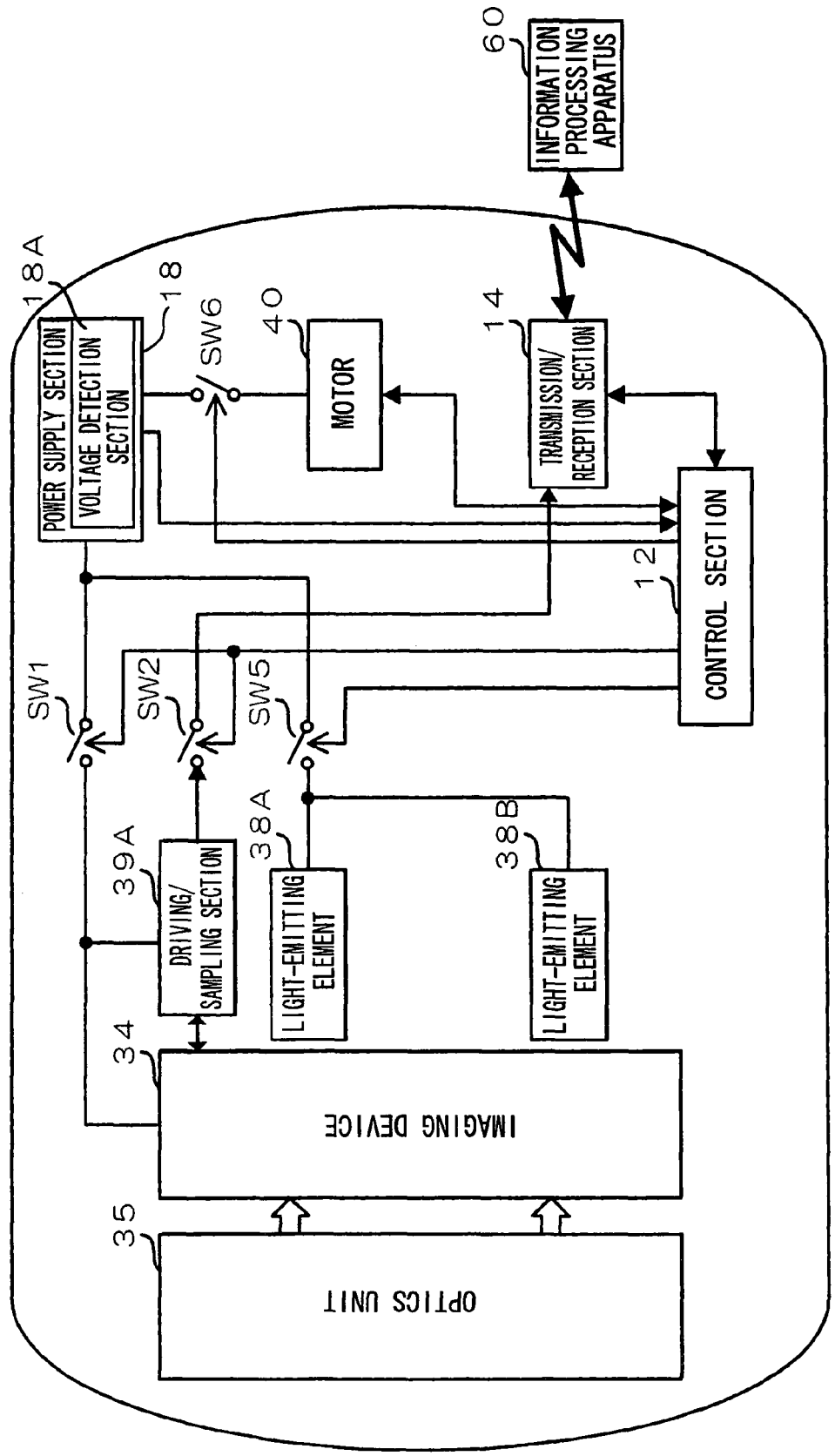
FIG. 8 is a block diagram showing principal structures of an electronic system of the capsule endoscope relating to the second embodiment.

As shown in FIG. 8, the capsule endoscope 10B relating to this second embodiment differs from the capsule endoscope 10 relating to the above-described first embodiment only in that the optics unit 35 is employed in place of the focusing optical system 36A and the focusing optical system 36B, the imaging device 34 is employed in place of the imaging device 34A and the imaging device 34B, and the driving/sampling section 39B, the switch SW3 and the switch SW4 have been eliminated.

In the capsule endoscope 10B relating to this second embodiment, the single driving/sampling section 39A drives the imaging device 34, samples image data representing a subject image that is outputted from the imaging device 34 as a result of the driving, and outputs the data without distinguishing between the imaging region 33A and the imaging region 33B.

The capsule endoscope 10B relating to the present embodiment incorporates a remote control function which enables execution of operations in accordance with instructions from the information processing apparatus 60 (here, a personal computer), which is provided with functions which enable wireless transmissions in compliance with the communications standard that the transmission/reception section 14 complies with.

Now, in the capsule endoscope 10B relating to the present embodiment, as operations which can be executed by the above-mentioned remote control function, two kinds of operation are employed: Operations for turning the imaging section 30B by a predetermined angle (here, 5°) in an instructed direction (a direction which is either of the clockwise direction and the anti-clockwise direction), and stereoscopic photography operations.

In the capsule endoscope 10B relating to the present embodiment, transmissions and receptions of various kinds of signals between the various sections provided at the circuit board 32 and the various sections provided at the control circuit board 20 are implemented wirelessly via wireless communications sections (not shown) which are provided at the respective circuit boards. However, this is not a limitation; if the range of rotation angles of the imaging section 30B is limited, modes are possible in which these communications are implemented by wire.

In the capsule endoscope 10B relating to the present embodiment, as the above-mentioned stereoscopic photography operations, either of a stereoscopic photography operation with visible light (below referred to as a first stereoscopic photography operation) and a stereoscopic photography operation with non-visible light (here, infrared light) (below referred to as a second stereoscopic photography operation) can be selectively employed in accordance with instructions from an external apparatus.

Figure 9:
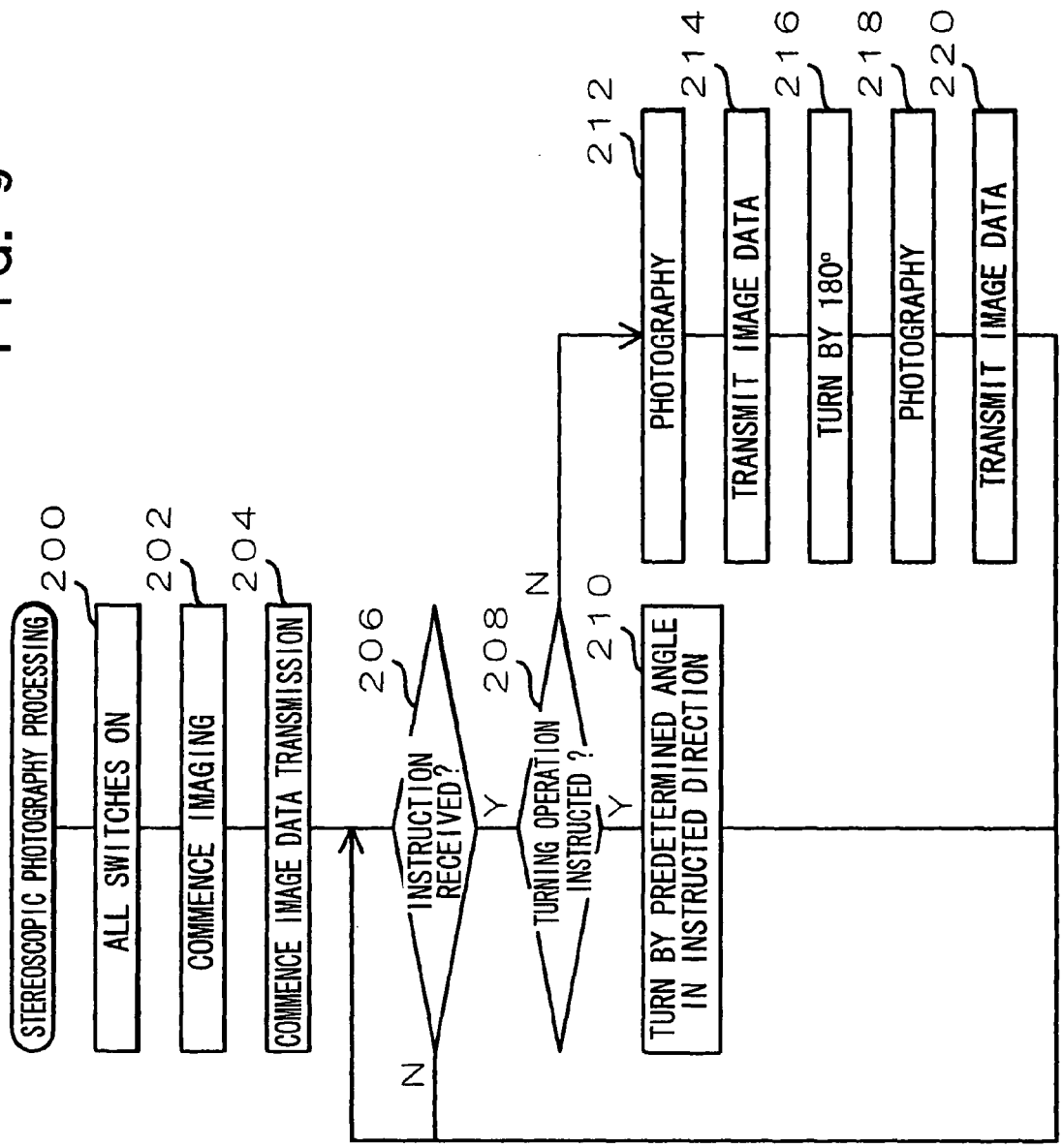
FIG. 9 is a flowchart showing a flow of processing of a stereoscopic photography processing program relating to the second embodiment.

Next, operation of the capsule endoscope 10B relating to this second embodiment will be described with reference to FIG. 9. FIG. 9 is a flowchart showing a flow of processing of a stereoscopic photography processing program which is executed by the control section 12 of the capsule endoscope 10B when a power switch (not shown) is set to an 'on' state. This program is memorized in advance at a memory (not shown) incorporated in the control section 12. Herein, in order to avoid complication, a case will be described in which whichever stereoscopic photography operation is to be employed, the first stereoscopic photography operation or the second stereoscopic photography operation, has been specified beforehand.

First, in step 200, all of the switches SW1, SW2, SW5 and SW6 are set to the connected state. Then, in step 202, the driving/sampling section 39A is controlled so as to commence an imaging operation by the imaging device 34. Hence, image data obtained by the imaging is outputted from the driving/sampling section 39A to the transmission/reception section 14 in real time.

Next, in step 204, the transmission/reception section 14 is controlled so as to transmit, in real time, only the image data obtained by the image region corresponding to the stereoscopic photography operation that has been specified beforehand (i.e., the imaging region 33A if the first stereoscopic photography operation has been specified and the imaging region 33B if the second stereoscopic photography operation has been specified).

The information processing apparatus 60 receives the image data, corresponding to the stereoscopic photography operation that has been specified, in real time by the processing described above. Accordingly, an image represented by the image data that is received is displayed in real time by the display section provided at the information processing apparatus 60.

Thus, a user can observe an image captured by the capsule endoscope 10B by referring to the image displayed at the display section. Hence, if a photographic angle of the captured image is not a required angle, the user operates the information processing apparatus 60 so as to transmit instruction information instructing rotation operations of the imaging section 30B, together with information representing the rotation direction, and so as to transmit information which instructs a stereoscopic photography operation when stereoscopic photography is to be performed.

Here, the transmission of image data representing a captured image which is commenced by the processing of the above-described step 202 and step 204 has the objective of display in real time. Therefore, the driving/sampling section 39A transmits the image data with the image data thinned by a predetermined pixel interval.

Next, in step 206, standby for reception of instruction information from the external apparatus is implemented. Then, in step 208, it is determined whether or not instruction information that is received is information instructing a rotation operation. If this determination is positive, the processing advances to step 210, the motor 40 is controlled such that the imaging section 30B turns by the predetermined angle in the turning direction indicated by the received information, and then the processing returns to step 206.

On the other hand, if the determination of step 208 is negative, the received instruction information is considered to be information instructing execution of a stereoscopic photography operation, the processing advances to step 212, and instruction information representing the execution of photography is sent to the driving/sampling section 39A. In response, the driving/sampling section 39A outputs image data obtained by the imaging device 34 to the transmission/reception section 14, without thinning.

Accordingly, in a next step 214, the transmission/reception section 14 is controlled so as to transmit only the image data obtained by the image region corresponding to the stereoscopic photography operation that has been specified beforehand (i.e., the imaging region 33A if the first stereoscopic photography operation has been specified and the imaging region 33B if the second stereoscopic photography operation has been specified).

Consequent to the above-described processing of step 212 and step 214, the information processing apparatus 60 receives the image data corresponding to the stereoscopic photography operation that has been specified. Hence, the image data that is received (below referred to as first image data) is saved to the memory section, such as a hard disk device, main memory or the like, provided at the information processing apparatus 60.

Next, in step 216, the motor 40 is controlled such that the imaging section 30B is turned by 180° with the rotation angle at this point in time as a reference point. Then, in step 218, similarly to the above-described step 212, instruction information designating the execution of photography is sent to the driving/sampling section 39A. In response, the driving/sampling section 39A outputs image data obtained by the imaging device 34 to the transmission/reception section 14, without thinning.

Next, in step 220, the transmission/reception section 14 is controlled so as to transmit only the image data obtained by the image region corresponding to the stereoscopic photography operation that has been specified beforehand (i.e., the imaging region 33A if the first stereoscopic photography operation has been specified and the imaging region 33B if the second stereoscopic photography operation has been specified). Thereafter, the processing returns to the aforementioned step 206.

Consequent to the above-described processing of step 218 and step 220, the information processing apparatus 60 receives image data which can constitute a stereoscopic image in combination with the first image data. Hence, the image data that is received (below referred to as second image data) is saved to the memory section, such as a hard disk device, main memory or the like, that is provided at the information processing apparatus 60.

Then, using the first image data and second image data which have been memorized to the memory section as described above, display and the like of a stereoscopic image photographed by the present stereoscopic photography processing program can be implemented. As it is, the second image data is an image which is vertically inverted relative to the image represented by the first image data. Therefore, when the second image data is being memorized to the memory section, or when the second image data which has been memorized to the memory section is to be used, this image is converted to a vertically inverted state thereof.

As has been described in detail hereabove, with the present embodiment, substantially the same effects as with the earlier described first embodiment can be realized. Additionally, the plural imaging devices of the present invention are integrally structured, and thus reductions in size and costs are possible.

In particular, with the present embodiment, because the plural imaging devices which are integrally structured are formed to have mutually different imaging sensitivity ranges, it is possible to realize stereoscopic photography with the plural mutually different imaging sensitivity ranges.

Further, with the present embodiment, because at least one of the different imaging sensitivity ranges includes a sensitivity range of non-visible light, stereoscopic photography with the non-visible light can be realized.

In the present embodiment, a condensing portion (here, the condensing optical systems 37A and 37B) is provided which focuses light emitted from a light-emitting element (here, the light-emitting elements 38A and 38B) toward a subject. Thus, light can be irradiated onto the subject more suitably.

Moreover, in the present embodiment, because the condensing portion and the focusing optical systems are integrally structured, further reductions in size and costs are possible.

Anyway, for the present embodiment, a case has been described in which, as the detectable wavelength ranges of the imaging device 34, the imaging region 33A employs a visible light region and the imaging region 33B employs a non-visible light region, and one or the other of a stereoscopic photography operation with visible light and a stereoscopic photography operation with non-visible light is selectively implemented. However, the present invention is not limited thus. For example, a mode is possible in which the detectable wavelength range of the imaging region 33B is a non-visible light region which includes a visible light region. By irradiating only visible light at a subject, it is possible to obtain a stereoscopic image with visible light using images that are captured by the imaging region 33A and the imaging region 33B, without performing the 180° rotation operation of the imaging section 30B. Alternatively, by irradiating only non-visible light at the subject and performing the 180° rotation operation of the imaging section 30B, it is possible to perform imaging twice with the imaging region 33B and thus obtain a stereoscopic image of non-visible light. In such a case, because it is possible to obtain a stereoscopic image of visible light by imaging once, these stereoscopic images can be obtained more easily and quickly than with the present embodiment.

Further, for the present embodiment, a case has been described in which the condensing optical system 37A and condensing optical system 37B are employed to focus the light emitted from the light-emitting element 38A and light-emitting element 38B onto the subject. However, the present invention is not limited thus. For example, a mode is possible in which a light diffusion system, for diffusing the light emitted from the light-emitting element 38A toward the subject, is employed instead of the condensing optical system 37A and a light diffusion system for diffusing the light emitted from the light-emitting element 38B toward the subject is employed instead of the condensing optical system 37B. Shapes, arrangements and the like of the light diffusion systems in such a mode may be exemplified by a case similar to the condensing optical systems 37A and 37B shown in FIG. 7A to FIG. 7C. In this case too, the light can be suitably irradiated at the subject.

Further, for the present embodiment, a case has been described in which either of the stereoscopic photography operation with visible light and the stereoscopic photography operation with non-visible light is selectively employed as a stereoscopic photography operation in accordance with instructions from an external apparatus. However, the present invention is not limited thus. For example, a mode is possible in which a visible light image and a non-visible light image are obtained by performing imaging with the imaging region 33A and the imaging region 33B simultaneously for the same subject, and then the imaging section 30B is turned by 180° and a visible light image and a non-visible light image are obtained by simultaneously performing imaging with the imaging region 33A and the imaging region 33B. Thus, both a stereoscopic image of visible light and a stereoscopic image of non-visible light can be obtained. A specific flow of processing for such a case may be exemplified by a mode in which, in the stereoscopic photography processing program shown as an example in FIG. 9, the transmission/reception section 14 is controlled in step 214 and in step 220 so as to transmit data obtained by both the imaging region 33A and the imaging region 33B. According to such a mode, both stereoscopic photography of visible light and stereoscopic photography of non-visible light can be implemented more quickly than in the present embodiment. Furthermore, because there is no need for imaging during the rotation driving by 180°, control for turning off the irradiating lights may be combined with the rotation driving. Accordingly, as a result of power for the irradiating lights being reassigned to power for rotation driving of the imaging section, power consumption can be smoothed.

Figure 10A:
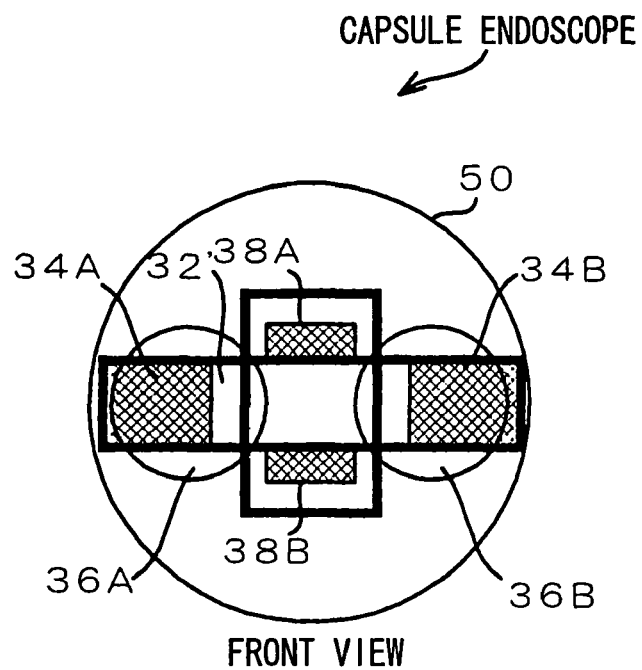
FIG. 10A is a front view showing a variant example of the circuit board employed in the capsule endoscope relating to the first embodiment.
Figure 10B:
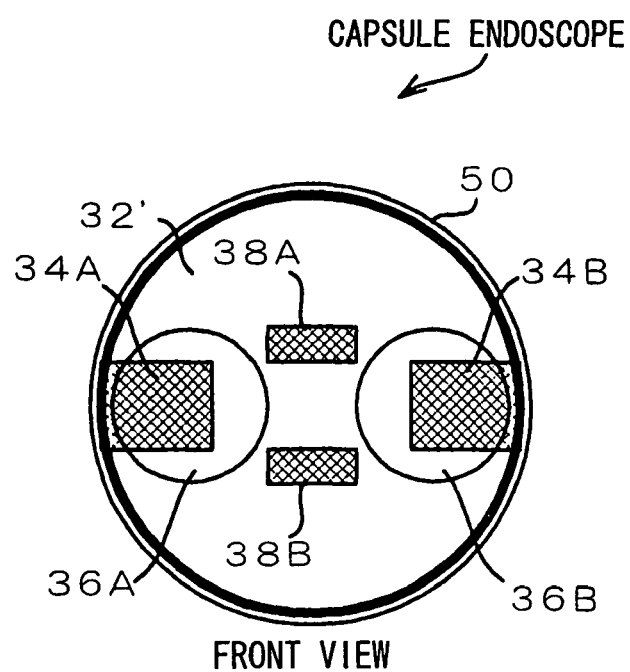
FIG. 10B is a front view showing a variant example of the circuit board employed in the capsule endoscope relating to the second embodiment.

Further, forms of the circuit boards 32 and 32B are not limited to the forms illustrated in the above-described first and second embodiments. For example, as shown in FIG. 10A, a mode is possible in which a rectangular shape is formed, at one end portion of which one imaging device 34A is disposed and at the other end portion of which the other imaging device 34B is disposed, with edges of the one end portion and the other end portion substantially fitting to the lengths of corresponding edges of the corresponding imaging devices. As a further example, as shown in FIG. 10B, a mode is possible in which the circuit board is circular. In such cases, the imaging devices can be disposed near to the outer peripheral face of the capsule endoscope, and thus photography of even nearer subjects can be implemented.

Further, a mode is possible in which processing for performing switching of an operation mode in accordance with a supply voltage from the power supply section 18, similarly to the first embodiment, is added to the stereoscopic photography processing program relating to the second embodiment. In such a case, excellent operations and power supply control can be implemented in accordance with supply voltages.

Furthermore, structures of the capsule endoscope relating to the embodiments described above (see FIG. 1A to FIG. 1C, FIG. 2, FIG. 5, FIG. 6, FIG. 7A to FIG. 7C, FIG. 8, FIG. 10A and FIG. 10B) are examples, and suitable modifications are possible within a scope not departing from the spirit of the present invention.

Further yet, the flows of processing of the stereoscopic photography processing programs described for the embodiments described above (see FIG. 4 and FIG. 9) are also examples. Modifications to the processing sequences of the steps, modifications to details of processing, deletions of unnecessary steps, additions of new steps, and the like can be implemented within a scope not departing from the spirit of the present embodiments.

What is claimed is:

1. A capsule endoscope comprising:
   a capsule housing;
   a plurality of imaging devices for respectively imaging a common subject;
   an imaging driving section that drives the plurality of imaging devices;
   a plurality of focusing optical systems that respectively correspond one-to-one with the plurality of imaging devices, each focusing optical system focusing an image of the subject at an imaging region of the corresponding imaging device;
   a control section that controls an imaging operation of the plurality of imaging devices by the imaging driving section;
   a rotating member provided so as to be rotatable about a predetermined rotation axis within the housing, the plurality of imaging devices being offset from the rotation axis and disposed at mutually different positions such that the plurality of imaging devices rotate about the rotation axis in accordance with rotation of the rotating member; and
   a rotation driving section that drives the rotation of the rotating member about the rotation axis,
   wherein each of the plurality of focusing optical systems is inclined such that an optical axis direction thereof is oriented forward in a direction of imaging by the plurality of imaging devices and toward a perpendicular direction that passes through a central point between the imaging regions of the plurality of imaging devices, and
   wherein the control section further controls a rotation operation of the rotating member by the rotation driving section.

2. The capsule endoscope of claim 1, wherein the plurality of imaging devices are provided within the housing such that central positions of the imaging regions are disposed at outer sides relative to optical axis centers of the corresponding focusing optical systems.

3. The capsule endoscope of claim 1, wherein the plurality of imaging devices is integrally structured.

4. The capsule endoscope of claim 3, wherein the integrally structured plurality of imaging devices comprises mutually different imaging sensitivity ranges.

5. The capsule endoscope of claim 4, wherein at least one of the different imaging sensitivity ranges comprises a sensitivity range of non-visible light.

6. The capsule endoscope of claim 1, further comprising a light-emitting element that irradiates light at the subject.

7. The capsule endoscope of claim 6, further comprising
   a condensing section that condenses light emitted from the light-emitting element toward the subject or
   a diffusion section that diffuses light emitted from the light-emitting element toward the subject.

8. The capsule endoscope of claim 7, wherein the focusing optical systems and the condensing section or the diffusion section are integrally structured.

9. The capsule endoscope of claim 6, wherein two of the light-emitting element are provided, one of the two light-emitting elements emitting visible light and the other light-emitting element emitting infrared light.

10. The capsule endoscope of claim 1, wherein the control section controls the rotation driving section so as to drive the rotating member to rotate within a range of rotation angle of 180°.

11. The capsule endoscope of claim 1, wherein the rotating member comprises a circuit board having a circular form, the imaging devices being disposed at vicinities of end portions of the circuit board.

12. The capsule endoscope of claim 1, wherein
   the plurality of imaging devices is two imaging devices, and
   the rotating member includes a circuit board having a rectangular form, at one end portion of which one of the imaging devices is disposed and at another end portion of which the other of the imaging devices is disposed, edges of the one end portion and the other end portion substantially matching lengths of corresponding edges of the imaging devices.

13. The capsule endoscope of claim 1, wherein the rotation driving section comprises a stepper motor.

14. The capsule endoscope of claim 1, wherein the imaging devices comprise a CCD area sensor.

15. A capsule endoscope comprising:
   a capsule housing;
   a plurality of imaging devices for respectively imaging a common subject;
   an imaging driving section that drives the plurality of imaging devices;
   a plurality of focusing optical systems that respectively correspond one-to-one with the plurality of imaging devices, each focusing optical system focusing an image of the subject at an imaging region of the corresponding imaging device;
   a control section that controls an imaging operation of the plurality of imaging devices by the imaging driving section;
   a power supply section that supplies power to the plurality of imaging devices and the plurality of imaging driving sections to separately drive corresponding sets of the imaging devices and the imaging driving sections; and
   a detection section that detects a voltage of power supplied by the power supply section,
   wherein each of the plurality of focusing optical systems is inclined such that an optical axis direction thereof is oriented forward in a direction of imaging by the plurality of imaging devices and toward a perpendicular direction that passes through a central point between the imaging regions of the plurality of imaging devices,
   wherein the imaging driving section is plurally provided such that a plurality of imaging driving sections respectively correspond one-to-one with the plurality of imaging devices, and
   wherein the control section controls such that an operation mode and a state of power supply from the power supply section are switched in accordance with a result of detection by the detection section.

16. The capsule endoscope of claim 15, wherein the plurality of imaging devices are provided within the housing such that central positions of the imaging regions are disposed at outer sides relative to optical axis centers of the corresponding focusing optical systems.

17. The capsule endoscope of claim 15, wherein the control section controls the power supply section such that,
   if the voltage detected by the detection section is higher than a predetermined threshold, power is supplied to all of the imaging devices and imaging driving sections and,
   if the detected voltage is less than or equal to the predetermined threshold, power is supplied to the respective sets of the imaging devices and the imaging driving sections in time divisions.

18. The capsule endoscope of claim 17, wherein the control section controls such that if the voltage detected by the detection section is less than or equal to a second predetermined threshold, which is lower than the predetermined threshold, power is supplied to only one of the sets of the imaging devices and the imaging driving sections.

19. The capsule endoscope of claim 15, further comprising a transmission section that transmits to outside capsule endoscope information representing an operation mode that is being employed.

20. The capsule endoscope of claim 15, further comprising a reception section that receives instruction information instructing an operation mode to be employed, wherein, when the instruction information is received by the reception section, the control section implements a control to switch the operation mode and state of power supply to the operation mode whose employment is instructed by the instruction information.

21. The capsule endoscope of claim 15, wherein the plurality of imaging devices is integrally structured.

22. The capsule endoscope of claim 21, wherein the integrally structured plurality of imaging devices comprises mutually different imaging sensitivity ranges.

23. The capsule endoscope of claim 22, wherein at least one of the different imaging sensitivity ranges comprises a sensitivity range of non-visible light.

24. The capsule endoscope of claim 15, further comprising a light-emitting element that irradiates light at the subject.

25. The capsule endoscope of claim 24, further comprising:
a condensing section that condenses light emitted from the light-emitting element toward the subject; or
a diffusion section that diffuses light emitted from the light-emitting element toward the subject.

26. The capsule endoscope of claim 25, wherein the focusing optical systems and the condensing section or the diffusion section are integrally structured.

27. The capsule endoscope of claim 24, wherein two of the light-emitting element are provided, one of the two light-emitting elements emitting visible light and the other light-emitting element emitting infrared light.

28. The capsule endoscope of claim 15, wherein the imaging devices comprise a CCD area sensor.

29. A capsule endoscope comprising:
a capsule housing;
a plurality of imaging devices for respectively imaging a common subject;
an imaging driving section that drives the plurality of imaging devices;
a plurality of focusing optical systems that respectively correspond one-to-one with the plurality of imaging devices, each focusing optical system focusing an image of the subject at an imaging region of the corresponding imaging device;
a control section that controls an imaging operation of the plurality of imaging devices by the imaging driving section;
a rotating member provided so as to be rotatable about a predetermined rotation axis within the housing, the plurality of imaging devices being offset from the rotation axis and disposed at mutually different positions such that the plurality of imaging devices rotate about the rotation axis in accordance with rotation of the rotating member; and
a rotation driving section that drives the rotation of the rotating member about the rotation axis,
wherein the plurality of imaging devices are provided within the housing such that central positions of the imaging regions are disposed at outer sides relative to optical axis centers of the corresponding focusing optical systems, and
wherein the control section further controls a rotation operation of the rotating member by the rotation driving section.

* * * * *